Figure 1:
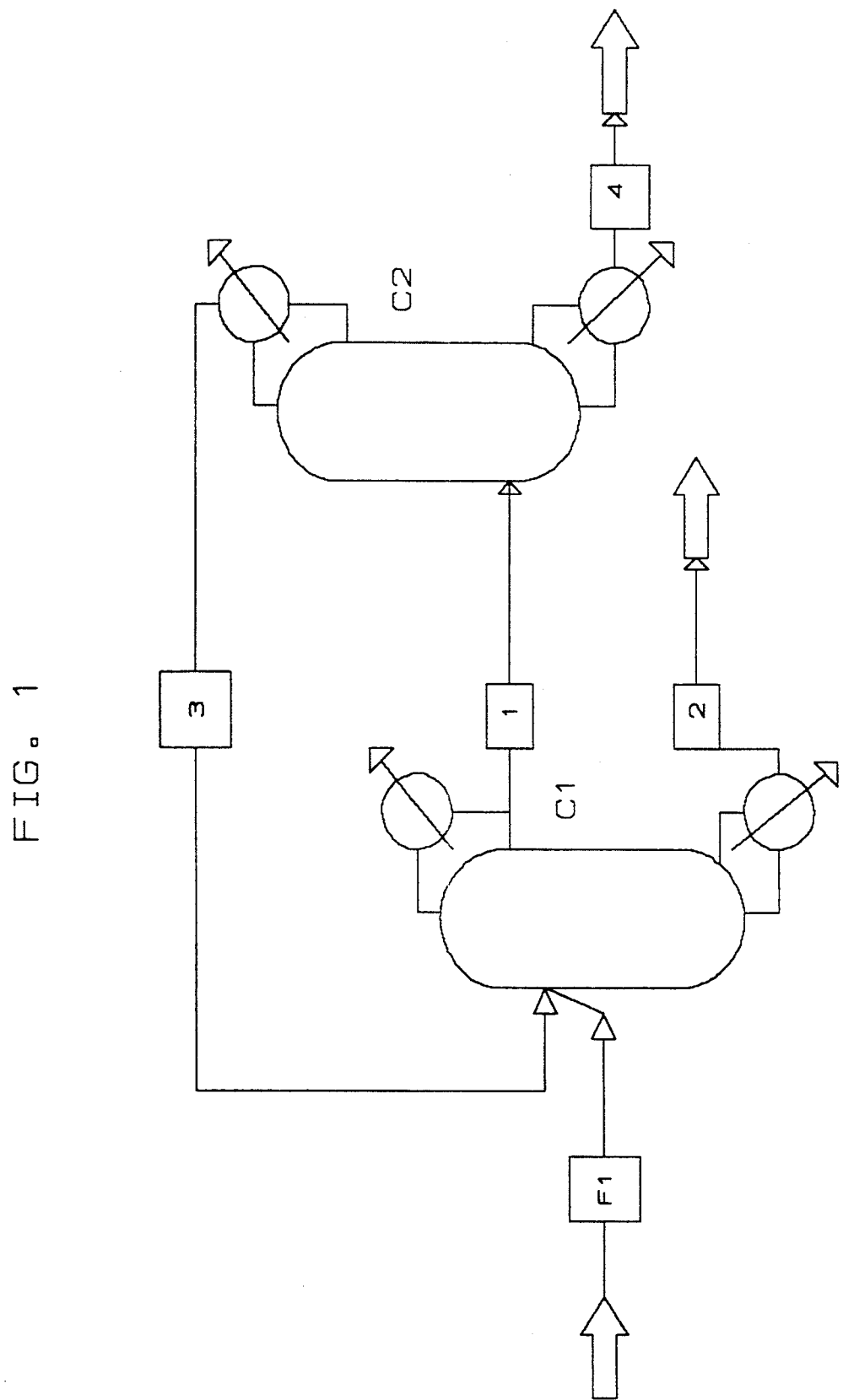

United States Patent [19]

Clemmer et al.

[11] Patent Number: 5,346,595
[45] Date of Patent: Sep. 13, 1994

[54] PROCESS FOR THE PURIFICATION OF A PENTAFLUOROETHANE AZEOTROPE

[75] Inventors: Paul G. Clemmer; Hsueh S. Tung; Addison M. Smith, all of Erie, N.Y.

[73] Assignee: AlliedSignal Inc., Morris Township, Morris County, N.J.

[21] Appl. No.: 23,827

[22] Filed: Feb. 23, 1993

[51] Int. Cl.$^5$ .......................... B01D 3/14; C07C 17/38
[52] U.S. Cl. ........................................ 203/75; 203/77; 203/82; 203/DIG. 11; 570/178
[58] Field of Search ................ 203/77, 74, 75, 91, 203/82, DIG. 19, DIG. 11; 570/178

[56] References Cited

U.S. PATENT DOCUMENTS

| | | | |
|---|---|---|---|
| 2,324,255 | 7/1943 | Britton et al. | 203/77 |
| 2,617,756 | 11/1952 | Eliot | 203/77 |
| 2,901,407 | 8/1959 | Colton | 203/78 |
| 2,998,357 | 8/1961 | Gillette et al. | 203/77 |
| 3,329,586 | 7/1967 | Pettingill | 203/78 |
| 3,505,233 | 4/1970 | Clark et al. | |
| 3,732,150 | 5/1973 | Bailey | 570/178 |
| 3,755,477 | 8/1973 | Firth et al. | |
| 4,362,603 | 12/1982 | Presson et al. | 203/77 |
| 5,087,329 | 2/1992 | Felix | |
| 5,158,652 | 10/1992 | Pucci et al. | 203/77 |

FOREIGN PATENT DOCUMENTS 53-39427  10/1978  Japan ................................ 203/77

Primary Examiner—Wilbur Bascomb, Jr.
Attorney, Agent, or Firm—Colleen D. Szuch; Jay P. Friedenson

[57] ABSTRACT

The invention generally relates to a process for the purification of a component of a binary azeotrope in which the composition of the azeotrope changes by about 10 mole percent with pressure comprising:

(a) subjecting a binary azeotrope to a distillation step in which most of one of the binary components is removed as distillate (distillate 1) with the bottoms (bottoms 1) enriched in the other component;

(b) subjecting distillate 1 to at least one additional distillation step conducted at a different pressure in which most of the component recovered as bottoms 1 is removed as distillate 2 with the bottoms 2 enriched in the component enriched in distillate 1;

(c) optionally repeating step (b) as many times as desired; and (d) recovering the desired purified component.

The invention is particularly useful in the purification of pentafluoroethane in a pentafluoroethane/chloropentafluoroethane azeotrope.

19 Claims, 1 Drawing Sheet

PROCESS FOR THE PURIFICATION OF A PENTAFLUOROETHANE AZEOTROPE

BACKGROUND OF THE INVENTION

Pentafluoroethane or HFC-125 is a stratospherically safe substitute for dichlorodifluoromethane (CFC-12) and chloropentafluoroethane (CFC-115) in refrigerant and sterilant gas applications. Methods for the production of HFC-125 are well known in the art. See, for example, U.S. Pat. No. 3,755,477. The problem with these processes is that they produce large amounts of CFC-115 as a by-product which must be removed in order to comply with the Program for Alternative Fluorocarbon Toxicity Testing (PAFT) guidelines for product purity. PAFT requires that no more than 0.5% CFC-115 can be present in HFC-125. In addition, still lower levels of CFC-115 (i.e., <0.5%) are desirable to eliminate any ozone depletion risk.

Because CFC-115 forms an azeotrope with HFC-125, see U.S. Pat. No. 3,505,233, it is hard to remove using conventional separation techniques such as simple distillation. The art has therefore looked to extractive distillation techniques to separate these materials. See U.S. Pat. No. 5,087,329 which utilizes a 1–4 carbon fluorocarbon which optionally contains hydrogen and/or chlorine and has a boiling point of $-39°$ C$<$e.a.$<50°$ C. to increase the relative volatility of HFC-125 so that it can be more easily removed from the mixture. The problem with extractive distillation is that it adds cost and time, requiring yet another distillation step to recover the extracting agent.

Applicants have discovered a process for the removal of CFC-115 from HFC-125 which overcomes these drawbacks and results in the production of high purity HFC-125 in high yield.

DESCRIPTION OF THE INVENTION

The invention preferably relates to a process for the purification of pentafluoroethane in a binary azeotrope of pentafluoroethane and chloropentafluoroethane comprising:

(a) subjecting a mixture comprising pentafluoroethane and at least about 0.5 mole % chloropentafluoroethane to a distillation step in which most of one of pentafluoroethane or chloropentafluoroethane is removed as distillate (distillate 1) with the bottoms (bottoms 1) enriched in the other component;

(b) subjecting distillate 1 to at least one additional distillation step conducted at a different pressure in which most of the component recovered as bottoms I is removed as distillate 2 with the bottoms 2 enriched in the component enriched in distillate 1;

(c) optionally repeating step (b) as many times as desired; and (d) recovering purified pentafluoroethane.

The invention is not limited to the purification of pentafluoroethane. It is generally applicable to the purification of any component of a binary azeotrope in which the composition of the azeotrope changes by about 10 mole percent with pressure and comprises:

(a) subjecting a binary azeotrope to a distillation step in which most of one of the binary components is removed as distillate (distillate 1) with the bottoms (bottoms 1) enriched in the other component;

(b) subjecting distillate 1 to at least one additional distillation step conducted at a different pressure in which most of the component recovered as bottoms 1 is removed as distillate 2 with the bottoms 2 enriched in the component enriched in distillate 1;

(c) optionally repeating step (b) as many times as desired; and (d) recovering the desired purified component.

We have discovered that by using the above-described novel distillation technique, we are able to minimize the effect of the CFC-115/HFC-125 azeotrope and produce high purity HFC-125 in high yield.

It is well known in the art that the composition of an azeotrope will vary with pressure. We discovered that the composition of the CFC-115/HFC-125 azeotrope changes dramatically (i.e., more than one would have predicted) with pressure. Specifically, we discovered that when pressure is increased to about 200 psia, the concentration of CFC-115 in the CFC-115/HFC-125 azeotrope approaches zero.

As stated above, the novel distillation technique of the invention is applicable to the purification of any component of a binary azeotrope in which the azeotrope composition changes by about 10 mole percent with pressure.

The purification of a component of a binary azeotrope, such as HFC-125 in the HFC-125/CFC-115 azeotrope, via the novel distillation technique of the invention may be accomplished by using a single distillation column operating at low and high pressure (or vice versa) with different batches or a series of distillation columns (i.e., two or more) operating at several different pressures. When a single distillation column is used, the crude HFC-125 mixture containing CFC-115 may be fed, for example, to a distillation column operating at high pressure. The distillate is then collected and re-fed into the column now cleaned and operating at low pressure. The purified HFC-125 is then recovered from the bottom of the still. See Example 1. Example 2 and FIG. 1, exemplify the novel distillation technique of the invention using two columns.

When two or more columns are used, they may be operated as a batch or continuous distillation. FIG. 1 is a schematic view of the novel distillation technique of the invention in which two distillation columns are used in a continuous distillation. In this figure, the distillate or overhead (3) from the low pressure column (C2) is recycled back to the high pressure column (C1). Alternately, the first distillation column may be operated at low pressure and the second column at high pressure. In this case, the distillate from the high pressure column is recycled to the low pressure column. When the novel distillation technique of the invention is used commercially, it is best to use it in the continuous operating mode in order to maximize the HFC-125 yield.

The precise configuration (i.e., whether the feed is first introduced into a high or low pressure column) depends upon the feed composition and process economics. The feed composition must contain less than the azeotropic amount of CFC-115 in order for the CFC-115 to be removed as distillate (overhead). For example, if the CFC-115 concentration in the feed is greater than the azeotropic composition in the low pressure column, then it will be necessary to introduce the feed into the high pressure column so that the majority of the CFC-115 can be removed quickly from the bottom of the high pressure column.

The pressure at which the distillations are conducted is preferably less than about 400 psia and greater than about 5 psia, more preferably less than about 300 psia and greater than about 10 psia, and most preferably less than about 250 psia and greater than about 15 psia. The distillations may for example be conducted at a pressure of from about 50 to about 400 psia and a pressure of from about 15 to about 35 psia, a pressure of from about 100 to about 300 psia and a pressure of from about 15 to about 25 psia, a pressure of from about 150 to about 250 psia and a pressure from about 15 to about 20 psia.

The pressure at which most of the HFC-125 can be removed as distillate is preferably about 50 to about 300 psia, more preferably about 100 to about 250 psia and most preferably about 150 to about 220 psia. The pressure at which most of the CFC-115 can be removed as distillate is preferably less than about 35 psia, more preferably less than about 25 psia and most preferably less than about 20 psia.

The temperature at which the distillation(s) is(are) conducted will depend on the pressure used.

The HFC-125 to be purified may be prepared by any process known in the art. See U.S. Pat. No. 3,755,477. Typically, known processes for the production of HFC-125 like that of U.S. Pat. No. 3,755,477 produce at least 2 mole % CFC-115 as a by-product.

EXAMPLE 1

Crude HFC-125 containing 98.5 mole % HFC-125, 1.2 mole % CFC-115 and about 0.3 mole % of other reaction products prepared by the fluorination of dichlorotrifluoroethane (i.e., 1,1-dichloro-2,2,2-trifluoroethane (HCFC-123) containing about 9 mole 1,2-dichloro-1,2,2-trifluoroethane (HCFC-123a)) with anhydrous hydrogen fluoride in the presence of a chromia/alumina catalyst was charged to a distillation column consisting of an Inconel reboiler attached to a 2 inch diameter stainless steel column filled with ¼" protruded ribbon packing made of Monel. A stainless steel condenser was mounted on top of the column. Chilled methanol was pumped to the condenser to provide cooling. The distillation column was operated at about 24.7 psia, a reflux temperature of about −38° C. and a reboiler temperature of about −37° C.

Upon distillation, a distillate containing about 95 mole % HFC-125 and about 5 mole % CFC-115 was removed at a reflux ratio of about 20:1 until the reboiler CFC-115 content was reduced to about 0.3 mole %. The distillate was then fed back into the column and distilled again. This time, the pressure in the distillation column was raised to about 206.7 psia by heating the reboiler using steam and lowering the condenser coolant flow. The reflux temperature was about 30° C. and the reboiler temperature was about 40° C. The distillate from this second distillation had a composition of about 97/3 mole % HFC-125/CFC-115 respectively.

EXAMPLE 2

The following Example is performed using the set-up shown in FIG. 1.

To a distillation column, C1, similar in structure to the distillation column of Example 1 is fed crude HFC-125 containing 20 mole % CFC-115 (see Table I, column F1) which is obtained by the hydrofluorination of HCFC-123 with anhydrous hydrogen fluoride in the presence of a chrome oxide catalyst. The distillation is conducted at 220 psia, a reflux temperature of about 28° C. and a reboiler temperature of about 35° C. The overhead (1) contains relatively pure HFC-125 (96 mole %). Little CFC-115 is carried overhead as the azeotrope while the bottom (2) is rich in CFC-115. The overhead is then passed to a second distillation column, C2, similar in structure to C1, operated at low pressure, (i.e., 24.7 psia), a reflux temperature of about −38° C. and a reboiler temperature of about −37° C. At low pressure, the amount of CFC-115 in the azeotrope increases dramatically. The azeotrope, now rich in CFC-115, is distilled over (3), while essentially pure HFC-125 (99.8 mole %) is removed as the bottoms (4). See Table I for an in depth description of the reaction conditions and mass balance information.

TABLE I

| Heat and Material Balance Table | | | | | |
|---|---|---|---|---|---|
| | Stream ID | | | | |
| | F1 | 1 | 2 | 3 | 4 |
| Mole Flow LBMOL/HR | | | | | |
| G125 | 0.80 | 1.04 | 0.35 | 0.27 | 0.77 |
| G115 | 0.20 | 0.04 | 0.19 | 0.04 | 1.19 E-3 |
| Total Flow LBMOL/HR | 1.00 | 1.08 | 0.23 | 0.31 | 0.77 |
| Total Flow LB/HR | 126.91 | 131.02 | 34.89 | 39.01 | 92.01 |
| Std. Vol Flow FT³/HR | 1.69 | 1.84 | 0.47 | 55.02 | 1.02 |
| Temp. °C. | 26.00 | 31.32 | 41.48 | −36.71 | −36.32 |
| Pressure PSIA | 220.00 | 214.70 | 214.70 | 24.70 | 24.70 |

EXAMPLE 3

Crude HFC-125 containing 98.5 mole % HFC-125, 1.2 mole % CFC-115 and about 0.3 mole % of other reaction products is prepared by the fluorination of dichlorotrifluoroethane (i.e., 1,1-dichloro-2,2,2-trifluoroethane (HCFC-123) containing about 9 mole % 1,2-dichloro-1,2,2-trifluoroethane (HCFC-123a)) with anhydrous hydrogen fluoride in the presence of a chromia/alumina catalyst and is charged to a distillation column consisting of an Inconel reboiler attached to a 2 inch diameter stainless steel column filled with ¼" protruded ribbon packing made of Monel. A stainless steel condenser is mounted on top of the column. Chilled methanol is pumped to the condenser to provide cooling. The distillation column is operated at about 180 psia, a reflux temperature of about 20° C. and a reboiler temperature of about 30° C.

Upon distillation, the distillate contains essentially pure HFC-125 (>99 mole %) while the bottom is enriched in CFC-115. The distillate is then fed back into the column and distilled at a pressure of about 35 psia (obtained by raising the condenser coolant flow), a reflux temperature of about −26° C. and a reboiler temperature of about −25° C. Under these conditions, the distillate is enriched in CFC-115 while the bottom contains essentially pure HFC-125 (>99.5 mole %). The distillate from the second distillation is then fed back into the column and distilled at a pressure of about 210 psia (obtained by heating the reboiler using steam and lowering the condenser coolant flow), a reflux temperature of about 25° C. and a reboiler temperature of about 32° C. Upon distillation, the overhead is essentially pure HFC-125 (>97 mole %) . CFC-115 (containing about 40 mole % HFC-125) is recovered as the bottom.

EXAMPLE 4

To a distillation column, similar to the distillation column of Example 3 is fed crude HFC-125 containing 2 mole % CFC-115 obtained by the hydrofluorination of HCFC-123 with anhydrous hydrogen fluoride in the presence of a chrome oxide catalyst. The distillation is conducted at about 30 psia, a reflux temperature of about −30° C. and a reboiler temperature of about −29° C. The overhead is enriched in CFC-115 (5 mole CFC-115) while the bottom contains essentially pure HFC-125 (>99 mole %). The distillate is then passed to a second distillation column similar to the first column in structure but operated at high pressure (i.e., about 200 psia), a reflux temperature of about 24° C. and a reboiler temperature of about 32° C. At this pressure, the distillate is enriched in HFC-125 (>97 mole %) while the bottoms contain more CFC-115 (>10 mole %). The distillate is then fed to a third distillation column similar in structure to the first column and operated at low pressure (i.e., about 25 psia), a reflux temperature of about −37° C. and a reboiler temperature of about −36° C. At this pressure, the distillate is becoming enriched in CFC-115 (about 7 mole %) while the bottoms are richer in HFC-125 (>99 mole %). Finally, the distillate from this third distillation is fed to a fourth distillation column similar in structure to the first column but operated at about 225 psia, a reflux temperature of about 30° C. and a reboiler temperature of about 42° C. Under these conditions, essentially pure HFC-125 (>97 mole %) is recovered as distillate while the bottoms are enriched in CFC-115 (>40 mole %).

What is claimed is:

1. A process for the purification of pentafluoroethane comprising:
   (a) subjecting a mixture comprising pentafluoroethane and at least about 0.5 mole % chloropentafluoroethane to a distillation step in which a composition enriched in one of pentafluoroethane or chloropentafluoroethane is removed as distillate 1 with a bottoms 1 being enriched in the other component and removed;
   (b) subjecting distillate 1 to at least one additional distillation step conducted at a different pressure in which the component enriched as bottoms 1 is removed as a distillate 2 and recycled as a feed to step (a), with a bottoms 2 being enriched in the component enriched in distillate 1 and removed;
   (c) optionally repeating step (a) and step (b) one or more times; and
   (d) recovering purified pentafluoroethane as either bottoms 1 or bottoms 2.

2. The process of claim 1 wherein said distillation steps are conducted in a single column.

3. The process of claim 1 wherein said distillation steps are conducted in two separate columns.

4. The process of claim 2 wherein step (c) is omitted.

5. The process of claim 4 wherein the first distillation step is conducted at a pressure of at least 50 psia and the second distillation is conducted at a lower pressure.

6. The process of claim 4 wherein said distillation steps are conducted at about 50 to about 300 psia and at less than about 35 psia respectively.

7. The process of claim 4 wherein said distillation steps are conducted at about 150 to about 220 psia and at less than about 20 psia respectively.

8. The process of claim 4 wherein the first distillation step is conducted at a pressure of less than about 35 psia and the second distillation is conducted at a higher pressure.

9. The process of claim 4 wherein said distillations are conducted at less than about 35 psia and from about 50 to about 300 psia respectively.

10. The process of claim 4 wherein said distillations are conducted at less than about 20 psia and from about 150 to about 220 psia respectively.

11. The process of claim 3 wherein said distillation steps are conducted as batch distillations steps.

12. The process of claim 3 wherein said distillation steps are conducted as a continuous distillation process.

13. The process of claim 3 wherein step (c) is omitted.

14. The process of claim 13 wherein the first distillation step is conducted at a pressure of at least 50 psia and the second distillation is conducted at a lower pressure.

15. The process of claim 13 wherein said distillation steps are conducted at about 50 to about 300 psia and at less than about 35 psia respectively.

16. The process of claim 13 wherein said distillation steps are conducted at about 150 to about 220 psia and at less than about 20 psia respectively.

17. The process of claim 13 wherein the first distillation step is conducted at a pressure of less than about 35 psia and the second distillation is conducted at a higher pressure.

18. The process of claim 13 wherein said distillation steps are conducted at less than about 35 psia and from about 50 to about 300 psia respectively.

19. The process of claim 13 wherein said distillations are conducted at less than about 20 psia and from about 150 to about 220 psia respectively.

* * * * *

UNITED STATES PATENT AND TRADEMARK OFFICE
CERTIFICATE OF CORRECTION

PATENT NO. : 5,346,595
DATED : September 13, 1994
INVENTOR(S) : Paul G. Clemmer et al.

It is certified that error appears in the above-identified patent and that said Letters Patent is hereby corrected as shown below:

Claim 9

Col. 6, line 21, "distillations" should read --distillation steps--.

Claim 10

Col. 6, line 24, "distillations" should read -- distillation steps--.

Claim 19

Col. 6, line 48, "distillations" should read --distillation steps--.

Signed and Sealed this

Ninth Day of January, 1996

Attest:

BRUCE LEHMAN

Attesting Officer     Commissioner of Patents and Trademarks